(12) United States Patent
Lo

(10) Patent No.: US 10,751,504 B2
(45) Date of Patent: Aug. 25, 2020

(54) SLEEP AID MACHINE

(71) Applicant: Ten Square Inc, Bethpage, NY (US)

(72) Inventor: Roger Lo, Bethpage, NY (US)

(73) Assignee: Ten Square Inc., Bethpage, NY (US)

( * ) Notice: Subject to any disclaimer, the term of this patent is extended or adjusted under 35 U.S.C. 154(b) by 99 days.

(21) Appl. No.: 16/104,986

(22) Filed: Aug. 20, 2018

(65) Prior Publication Data

US 2020/0054854 A1 Feb. 20, 2020

(51) Int. Cl.
*A61M 21/02* (2006.01)
*A61N 2/00* (2006.01)
*A61N 2/02* (2006.01)
*A61M 21/00* (2006.01)

(52) U.S. Cl.
CPC .............. *A61M 21/02* (2013.01); *A61N 2/004* (2013.01); *A61N 2/02* (2013.01); *A61M 2021/0055* (2013.01)

(58) Field of Classification Search
CPC .......... A61M 21/02; A61M 2021/0055; A61N 2/004; A61N 2/02
USPC ............................................ 600/26–28, 9–15
See application file for complete search history.

(56) References Cited

U.S. PATENT DOCUMENTS

| | | | | |
|---|---|---|---|---|
| 4,723,536 A * | 2/1988 | Rauscher | ................. | A61N 2/02 600/14 |
| 6,004,257 A * | 12/1999 | Jacobson | ................. | A61N 2/02 600/9 |
| 6,203,486 B1 * | 3/2001 | Miller | ...................... | A61N 2/02 600/9 |
| 7,819,794 B2 * | 10/2010 | Becker | ..................... | A61N 2/02 600/14 |
| 8,517,909 B2 * | 8/2013 | Honeycutt | ............... | A61N 2/02 600/14 |
| 9,649,502 B2 * | 5/2017 | Phillips | .................... | A61N 2/02 |
| 2006/0281543 A1 * | 12/2006 | Sutton | ..................... | G07F 17/32 463/29 |
| 2010/0121131 A1 * | 5/2010 | Mathes | .............. | A61H 23/0236 600/14 |
| 2010/0298624 A1 * | 11/2010 | Becker | ................... | A61N 2/008 600/13 |
| 2015/0150745 A1 * | 6/2015 | Strlek | .................... | A61H 7/001 601/53 |
| 2017/0072210 A1 * | 3/2017 | Gangwish | ................ | A61N 7/00 |
| 2018/0154105 A1 * | 6/2018 | Bode | ..................... | A61M 21/02 |
| 2018/0168485 A1 * | 6/2018 | Chen | .................... | A61B 5/1113 |

\* cited by examiner

*Primary Examiner* — Navin Natnithithadha
*Assistant Examiner* — Sunita Reddy
(74) *Attorney, Agent, or Firm* — Alan D. Kamrath; Karin L. Williams; Mayer & Williams

(57) ABSTRACT

A sleep aid machine includes a housing, a base mounted on a lower portion of the housing, a top cover mounted on an upper portion of the housing, a main control module mounted in the housing, and an electromagnetic module mounted in the housing. The electromagnetic module is electrically connected with the main controller of the main control module. Thus, the electromagnetic module transmits electromagnetic waves with a specified frequency, so as to release and comfort the user, thereby helping the user sleep easily and comfortably.

8 Claims, 4 Drawing Sheets

SLEEP AID MACHINE

BACKGROUND OF THE INVENTION

1. Field of the Invention

The present invention relates to an electronic apparatus and, more particularly, to a sleep aid device or a sleep aid machine that transmits electromagnetic waves.

2. Description of the Related Art

In the modern world, people sometimes have difficulty falling asleep for various reasons. For example, adults are troubled by the pressure of daily life or work. Besides, infants and young children also express moods through crying when they are disturbed by external factors (such as noises) of the ambient environment or when they have physiological needs, so that sleep of the parents are also disturbed. While adults may take medicine, such as sleeping pills or the like, to help they sleep. However, the medicine may have a negative effect during a long period of time. The infants and young children can sleep by pacifying. However, it takes a lot of time for the parents to pacify the infants or young children.

BRIEF SUMMARY OF THE INVENTION

The primary objective of the present invention is to provide a sleep aid machine that transmits electromagnetic waves with a specified frequency, so as to help the user sleep.

In accordance with the present invention, there is provided a sleep aid machine comprising a housing, a base mounted on a lower portion of the housing, a top cover mounted on an upper portion of the housing, a main control module mounted in the housing, and an electromagnetic module mounted in the housing. The housing includes a housing body, a plurality of positioning blocks mounted in the housing body and spaced from each other, and two support blocks mounted in the housing body and located between the positioning blocks. The housing body of the housing is provided with a first wire hole located between the two support blocks. The two support blocks are spaced from one another. The base includes a base body having a top provided with a second wire hole. The main control module includes a main controller secured in the housing body of the housing, a connecting wire having a first end connected with the main controller, and a connector connected with a second end of the connecting wire. The connecting wire extends between the positioning blocks, between the two support blocks, through the first wire hole of the housing and through the second wire hole of the base. Thus, the connector is exposed outward from the housing. The electromagnetic module transmits electromagnetic waves and is electrically connected with the main controller of the main control module. The electromagnetic module is secured on the two support blocks of the housing and positioned between the positioning blocks.

According to the primary advantage of the present invention, the electromagnetic module transmits a Schumann wave, with a frequency of 7.83 Hz, to the ambient environment, so as to release and comfort the user, thereby helping the user sleep easily and comfortably, without needing aid of medicine.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
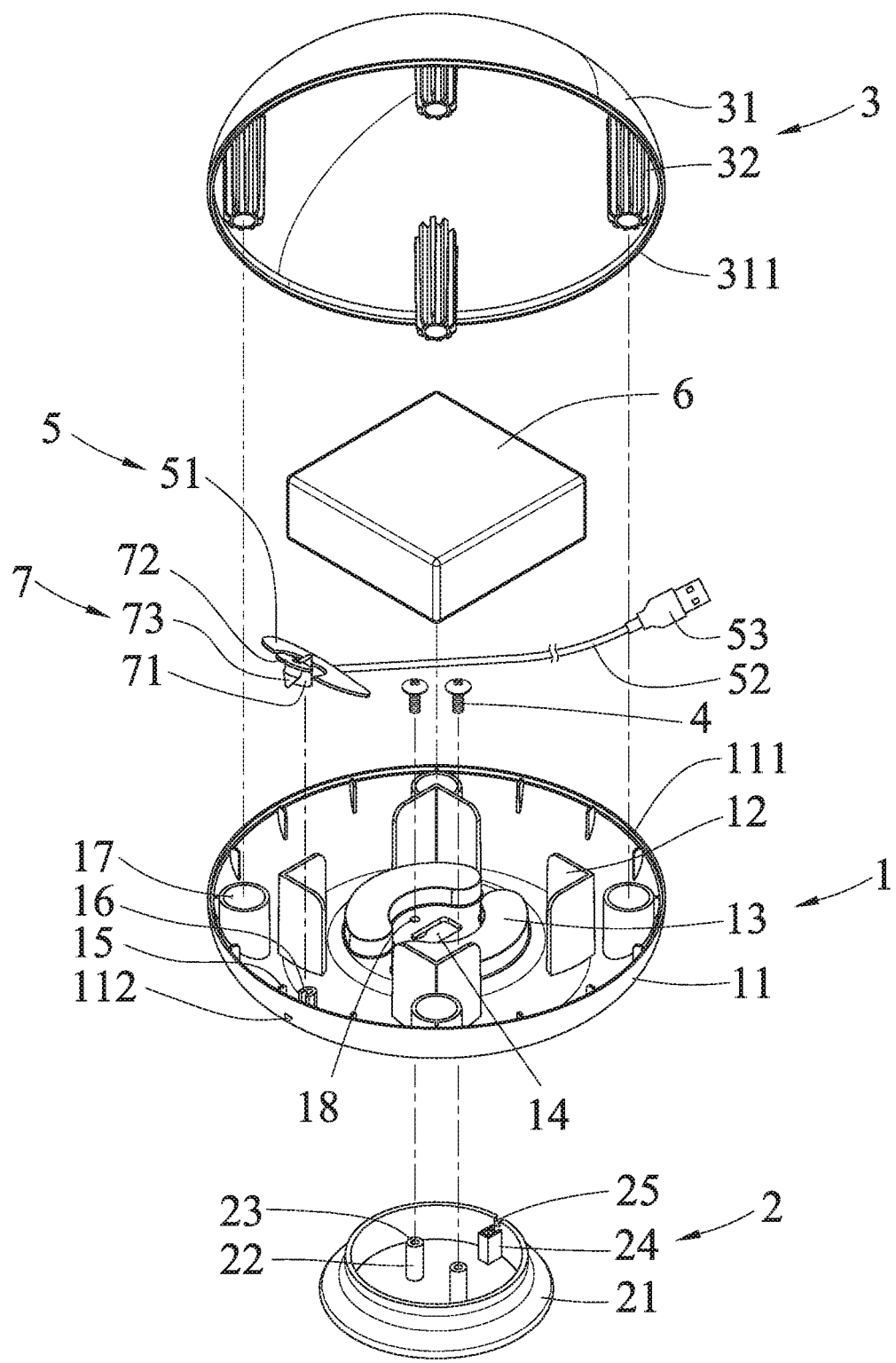
FIG. 1 is an exploded perspective view of a sleep aid machine in accordance with the preferred embodiment of the present invention.
Figure 2:
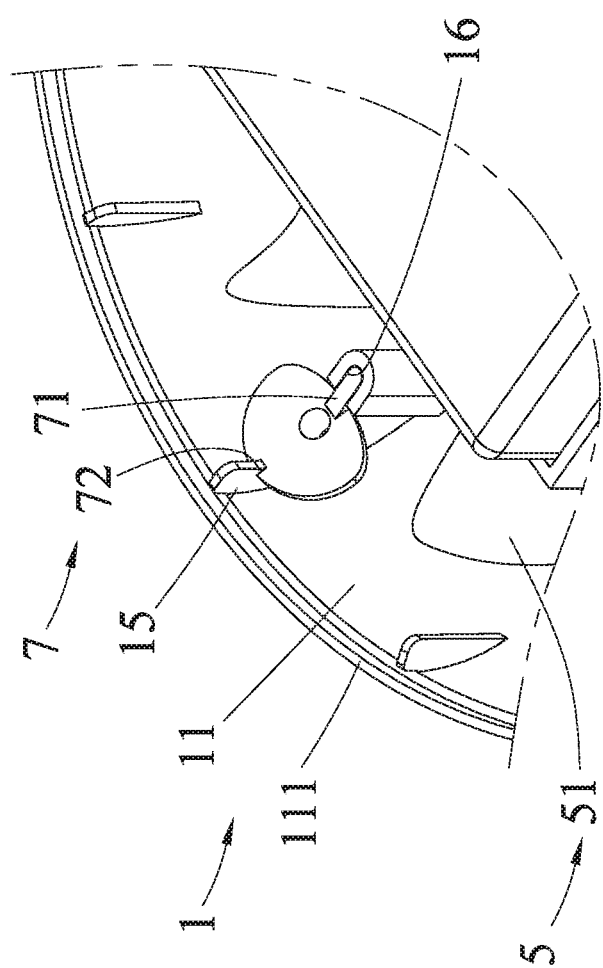
FIG. 2 is a partially enlarged perspective assembly view of the sleep aid machine in accordance with the preferred embodiment of the present invention.
Figure 3:
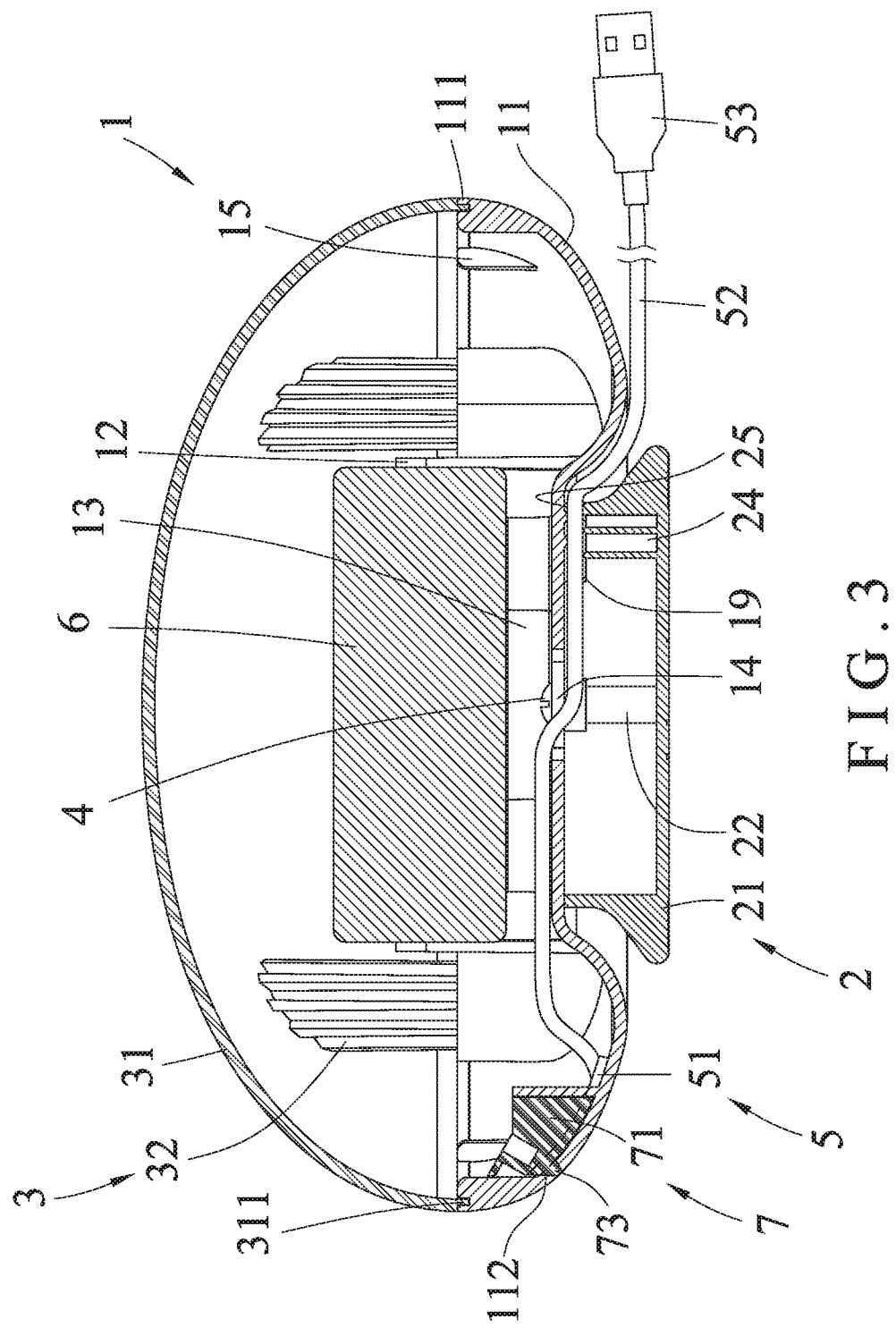
FIG. 3 is a cross-sectional assembly view of the sleep aid machine in accordance with the preferred embodiment of the present invention.

Referring to FIGS. 1-4, a sleep aid machine in accordance with the preferred embodiment of the present invention comprises a housing 1, a base 2 mounted on a lower portion of the housing 1, a top cover 3 mounted on an upper portion of the housing 1, a main control module 5 mounted in the housing 1, and an electromagnetic module 6 mounted in the housing 1.

The housing 1 includes a housing body 11, a plurality of (preferably four) positioning blocks 12 mounted in the housing body 11 and spaced from each other to define a predetermined space, and two support blocks 13 mounted in the housing body 11 and located between the positioning blocks 12. The housing body 11 of the housing 1 is provided with a first wire hole 14 located between the two support blocks 13. The two support blocks 13 are spaced from one another.

The base 2 includes a base body 21 having a top provided with a second wire hole 25.

The main control module 5 includes a main controller 51 secured in the housing body 11 of the housing 1, a connecting wire 52 having a first end connected with the main controller 51, and a connector 53 connected with a second end of the connecting wire 52. The connecting wire 52 extends between the positioning blocks 12, between the two support blocks 13, through the first wire hole 14 of the housing 1 and through the second wire hole 25 of the base 2. Thus, the connector 53 is exposed outward from the housing 1. Preferably, the connector 53 of the main control module 5 is a USB plug or the like.

The electromagnetic module 6 transmits electromagnetic waves and is electrically connected with the main controller 51 of the main control module 5. The electromagnetic module 6 is secured on the two support blocks 13 of the housing 1 and positioned between the positioning blocks 12. It is appreciated that, the connecting wire 52 of the main control module 5 initially passes between the positioning blocks 12, then passes between the two support blocks 13, and then passes through the first wire hole 14 of the housing 1, so that the electromagnetic module 6 will not press the connecting wire 52.

In the preferred embodiment of the present invention, an indicator module 7 is mounted in the housing 1 and is electrically connected with the main controller 51 of the main control module 5.

In the preferred embodiment of the present invention, the housing body 11 of the housing 1 is provided with at least one protrusion 15, a slot 16 located beside the at least one protrusion 15, and an indication hole 112 located beside the slot 16. The indicator module 7 includes an insert 71 inserted into the slot 16 of the housing 1 and an indication light 73 secured on the insert 71. The insert 71 of the indicator module 7 is provided with an insert hole 72, and the at least one protrusion 15 of the housing 1 is inserted into the insert hole 72 of the insert 71. The indication light 73 of the indicator module 7 is inserted into the indication hole 112 of the housing 1 and is electrically connected with the main controller 51 of the main control module 5.

In the preferred embodiment of the present invention, the housing body 11 of the housing 1 has a bottom provided with a plurality of (preferably two) mounting holes 18. The base 2 includes a plurality of (preferably two) posts 22 mounted on the base body 21 and inserted into the mounting holes 18 of the housing 1. Each of the posts 22 of the base 2 is provided with a fastening hole 23. The sleep aid machine further comprises a plurality of (preferably two) fastening members 4 extending through the mounting holes 18 of the housing 1 and secured in the fastening holes 23 of the posts 22.

Figure 4:
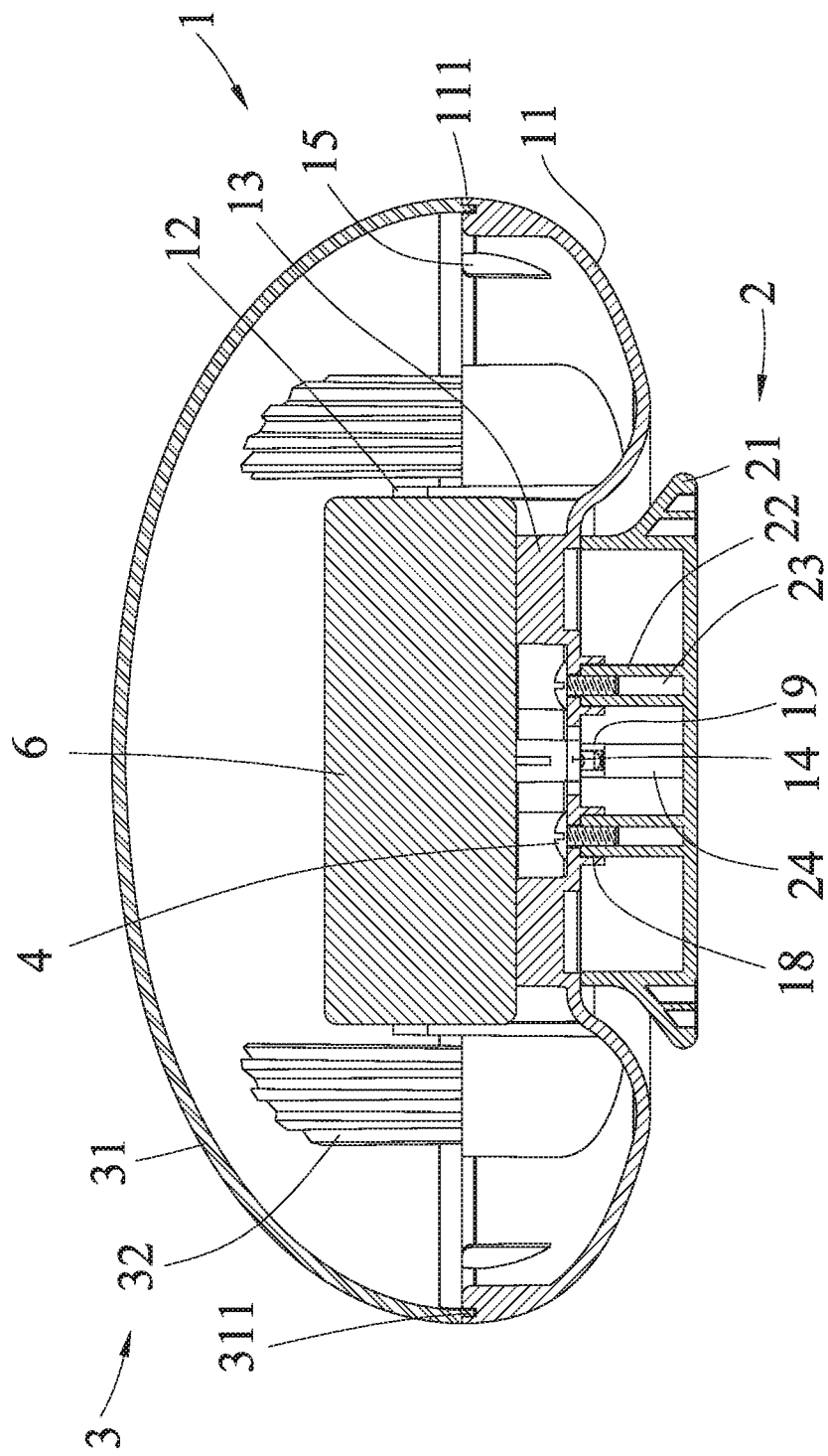
FIG. 4 is another cross-sectional assembly view of the sleep aid machine in accordance with the preferred embodiment of the present invention.

In practice, each of the fastening members 4 is a screw, and each of the fastening holes 23 of the posts 22 is a screw hole. As shown in FIG. 4, each of the mounting holes 18 of the housing 1 has a stepped shape and has an upper section with a smaller diameter and a lower section with a larger diameter. Thus, when the posts 22 of the base 2 are inserted into the mounting holes 18 of the housing 1, the posts 22 of the base 2 are stopped by an intersection of the upper section and the lower section of each of the mounting holes 18.

In the preferred embodiment of the present invention, the housing body 11 of the housing 1 is provided with a plurality of (preferably four) wells 17. The top cover 3 includes a cover body 31 covering the housing body 11 of the housing 1 and a plurality of (preferably four) columns 32 mounted on the cover body 31 and inserted into the wells 17 of the housing 1.

In the preferred embodiment of the present invention, the columns 32 of the top cover 3 and the wells 17 of the housing 1 are affixed to each other by adhesive.

In the preferred embodiment of the present invention, the housing body 11 of the housing 1 has a periphery provided with a first annular wall 111, and the cover body 31 of the top cover 3 has a periphery provided with a second annular wall 311 mounted on the first annular wall 111 of the housing 1. Preferably, the housing body 11 of the housing 1 is provided with a plurality of protrusions 15 located beside the first annular wall 111.

In the preferred embodiment of the present invention, the electromagnetic waves transmitted by the electromagnetic module 6 have a frequency of 7.83 Hz. It is appreciated that, the electromagnetic wave with a frequency of 7.83 Hz is called a Schumann resonance or wave.

In the preferred embodiment of the present invention, the bottom of the housing body 11 of the housing 1 is provided with two first abutting pieces 19 spaced with a predetermined distance. The base body 21 of the base 2 is provided with a second abutting piece 24 abutting the two first abutting pieces 19 of the housing 1. The second wire hole 25 of the base 2 is located beside the second abutting piece 24 and located between the two first abutting pieces 19 of the housing 1. The connecting wire 52 in turn extends between the positioning blocks 12, between the two support blocks 13, through the first wire hole 14 of the housing 1, between the two first abutting pieces 19 of the housing 1, and through the second wire hole 25 of the base 2.

In use, the connector 53 of the main control module 5 is a USB plug and is used to perform a charging function. The main controller 51 of the main control module 5 has a wireless connecting function (such as by Bluetooth connection). Thus, the user uses a mobile apparatus, such as a cell phone or the like, to connect the main controller 51, so as to control operation of the electromagnetic module 6. In such a manner, the electromagnetic module 6 is operated to transmit the Schumann wave with a frequency of 7.83 Hz, so as to release and comfort the user, thereby helping the user sleep. In addition, the main controller 51 of the main control module 5 changes the lighting state of the indication light 73 to remind the user of operation of the electromagnetic module 6. For example, when the electromagnetic module 6 is turned on, the indication light 73 is turned on by the main controller 51 and emits light, and when the electromagnetic module 6 is turned off, the indication light 73 is turned off by the main controller 51.

Accordingly, the electromagnetic module 6 transmits the Schumann wave to the ambient environment, so as to release and comfort the user, thereby helping the user sleep comfortably, and thereby enhancing the user's sleep quality by a deep sleeping.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the scope of the invention.

The invention claimed is:

1. A sleep aid machine configured to aid sleep in a user comprising:
    a housing;
    a base mounted on a lower portion of the housing;
    a top cover mounted on an upper portion of the housing;
    a main control module mounted in the housing; and
    an electromagnetic module mounted in the housing;
    wherein:
    the housing includes a housing body, a plurality of positioning blocks mounted in the housing body and spaced from each other, and two support blocks mounted in the housing body and located between the positioning blocks;
    the housing body of the housing is provided with a first wire hole located between the two support blocks;
    the two support blocks are spaced apart a fixed distance from one another;
    the base includes a base body having a top provided with a second wire hole;
    the main control module includes a main controller secured in the housing body of the housing, a connecting wire having a first end connected with the main controller, and a connector connected with a second end of the connecting wire;
    the connecting wire extends between the positioning blocks, between the two support blocks, through the first wire hole of the housing and through the second wire hole of the base;
    the connector is exposed outward from the housing;
    the electromagnetic module transmits electromagnetic waves at a specified frequency and, wherein the electromagnetic module is electrically connected with the main controller of the main control module;

the electromagnetic module is secured on the two support blocks of the housing and positioned between the positioning blocks; and wherein exposure of the user to the electromagnetic waves transmitted by the electromagnetic module aid the sleep in the user.

2. The sleep aid machine of claim 1, wherein an indicator module is mounted in the housing and is electrically connected with the main controller of the main control module.

3. The sleep aid machine of claim 2, wherein:
the housing body of the housing is provided with at least one protrusion, a slot located beside the at least one protrusion, and an indication hole located beside the slot;
the indicator module includes an insert inserted into the slot of the housing and an indication light secured on the insert;
the insert of the indicator module is provided with an insert hole;
the at least one protrusion of the housing is inserted into the insert hole of the insert; and
the indication light of the indicator module is inserted into the indication hole of the housing and is electrically connected with the main controller of the main control module.

4. The sleep aid machine of claim 1, wherein:
the housing body of the housing has a bottom provided with a plurality of mounting holes;
the base includes a plurality of posts mounted on the base body and inserted into the mounting holes of the housing;
each of the posts of the base is provided with a fastening hole; and
the sleep aid machine further comprises a plurality of fastening members extending through the mounting holes of the housing and secured in the fastening holes of the posts.

5. The sleep aid machine of claim 1, wherein the housing body of the housing is provided with a plurality of wells, and the top cover includes a cover body covering the housing body of the housing and a plurality of columns mounted on the cover body and inserted into the wells of the housing.

6. The sleep aid machine of claim 5, wherein the columns of the top cover and the wells of the housing are affixed to each other by adhesive.

7. The sleep aid machine of claim 5, wherein the housing body of the housing has a periphery provided with a first annular wall, and the cover body of the top cover has a periphery provided with a second annular wall mounted on the first annular wall of the housing.

8. The sleep aid machine of claim 1, wherein the electromagnetic waves transmitted by the electromagnetic module have a frequency of 7.83 Hz.

* * * * *